United States Patent [19]
Greene

[11] Patent Number: 6,100,377
[45] Date of Patent: *Aug. 8, 2000

[54] CONSTRAINED PEPTIDES

[75] Inventor: Mark I. Greene, Penn Valley, Pa.

[73] Assignee: The Trustees of the University of Pennsylvania, Philadelphia, Pa.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/257,783

[22] Filed: Jun. 10, 1994

[51] Int. Cl.$^7$ ............................... C07K 7/64; C07K 9/00
[52] U.S. Cl. .......................... 530/317; 530/326; 530/327; 530/328; 530/329; 514/9; 514/13; 514/14; 514/15; 514/16
[58] Field of Search .................................. 514/16, 17, 12, 514/14, 9, 15, 13; 530/328, 329, 326, 317

[56] References Cited

PUBLICATIONS

Rudinger, J 'Characteristics of amino acids as components of peptide hormones sequence'in Peptide Hormones, (ed. J.A. PArsons). University Park Press, Baltimore, pp. 1–7, 1976.
Mierke, D. et al., "Cis/Trans Isomers in Cyclic Peptides without N–Substituted Amides", *J. Am. Chem. Soc.* 1989, 111, 6847–6849.
Nutt, R. et al., "Side Chain Conformations of Somatostatin Analogs When Bound to Receptors", from "Somatostatin", Reichlin, S. Ed., Plenum Publishing Corp., 1987, pp. 83–88.
Pelton, J. et al., "Design and Synthesis of Conformationally Constrained Somatostatin Analogues with High Potency and Specificity for μ Opioid Receptors", *J. Med. Chem.* 1986, 29, 2370–2375.
Rivier, J. et al., "Tyrosylated Analogues of Somatostatin", *J. of Med. Chem.* 1976, 19(8), 1010–1013.
Taylor, J. et al., "In Vitro and in vivo Inhibition of Human Small Cell Lung Carcinoma (NCI–H69) Growth by a Somatostatin Analogue", Biochem. and Biophys. Res. Comm. 1988, 153(1), 81–86.
Amit et al, Science, vol. 233, Aug. 15, 1986, pp. 747–755.
Saragovi et al, Immunomethods, 1, 5–9 (1992).
Amit, et al., "Three–Dimensional Structure of an Antigen–Antibody Complex at 2.8 ÅResolution"Science 233: 747–753 (1986).
Bach, et al., "Structural Studies of a Family of High Affinity Ligands for GP$^{IIb/IIIa}$"New Adv. Peptidomimetics Small Mol. Design I: 1–26 (1994).
Bjorkman et al., "Structure of the Human Class I Histocompatiblity Antigen, HLA–A2"Nature 329: 506–511 (1987).
Cammarota et al., "Identification of a CD4 Binding Site on the β$^2$Domain of HLA–DR Molecules", Nature 356: 799–800 (1992).

Carroll et al., "Anti–I–A Antibody Modulation of Lymphocyte Traffic in Hapten–Stimulated Inbred Mice"Immunology 62: 471–475 (1987).
Chen et al., "Design and Synthesis of a CD4 β–turn Mimetic That Inhibits Human Immunodeficiency Virus Envelope Glycoprotein gp120 Binding and Infection of Human Lymphocytes", Proc. Nat'l. Acad. Sci. U.S.A. 89: 5872–5876 (1992).
Clayton et al., "Substitution of Murine for Human CD4 Residues Identifies Amino Acids Critical for HIV–gp120 Binding", Nature 335: 363–366 (1988).
Clayton et al., "Identification of Human CD4 Residues Affecting Class II MHC Versus HIV–1 gp120 Binding", Nature 339 : 548–551 (1989).
Davies and Padlan, "Antibody–Antigen Complexes"Annu. Rev. Biochem.: 439–473 (1990).
Di Blasio et al., "Noncoded Residues as Building Blocks in the Design of Specific Secondary Structures: Symmetrically Disubstituted Glycines and β–Alanine", Biopolymers 33: 1037–1049 (1993).
Doyle and Strominger, "Interaction Between CD4 and Class II MHC Molecules Mediates Cell Adhesion"Nature 330: 256–259 (1987).
Fink et al., "Correlations Between T–Cell Specificity and the Structure of the Antigen Receptor", Nature 321: 219–226 (1986).
Fleury et al., "Mutational Analysis of the Interaction Between CD4 and Class II MHC: Class II Antigens Contact CD4 on a Surface Opposite the gp120–Binding SIte", Cell 66: 1037–1049 (1991).
Habeeb, A. F. S. A, "Reaction of Protein Sulfhydryl Groups with Ellman's Reagent", Methods in Enzymology 25: 457–464 (1972).
Helms and Wetzel, "Proteolytic Excision and in Situ Cyclization of A Bioactie Loop in an REI–RGD Presentation Scaffold", Macromolecular Sciences Dept.
Hruby, "Conformational and Topographical Considerations in the Design of Biologically Active Peptides", Biopolymers 33: 1073–1082 (1993).
Kappler et al., "A T Cell Receptor vβSegment That Imparts Reactivity to a Class II Major Histocompatibility Complex Product", Cell 49: 263–271 (1987).
König et al ., "MHC Class II Interaction with CD4 Mediated by a Region Analogous to the MHC Class I Binding Site for CD8", Nature 356: 796–798 (1992).
Leahy et al., "Crystal Structure of a Soluble Form of the Human T Cell Coreceptor CD8 at 2.5 ÅResolution "Cell 68: 1145–1162 (1992).

(List continued on next page.)

*Primary Examiner*—Cecilia J. Tsang
*Assistant Examiner*—Anish Gupta
*Attorney, Agent, or Firm*—Pennie & Edmonds LLP

[57] ABSTRACT

Constrained peptides are disclosed which have cyclic portions that contain biologically active regions linked to two linear extensions that each comprise at least one aromatic-group containing amino acid residue. The constrained peptides of the invention are biologically active.

16 Claims, No Drawings

OTHER PUBLICATIONS

Levi et al., "A Complementarity–Determining Region Synthetic Peptide Acts as a Miniantibody and Neutralizes Human Immunodeficiency Virus Type 1 In Vitro", Proc. Natl. Acad., Sci. USA 90 : 437–408 (1993).

Lowry et al., "Genetically Restricted Antigen Presentation for Immunological Tolerance and Suppression", Nature 308: 373–374 (1984).

Manning et al., "Design of Cyclic and Linear Peptide Antagonists of Vasopression and Oxytocin: Current Status Future Directions" Reg. Peptides, 45:279–283 (1993).

Marshall et al., "Ch. 24, Peptide Conformation and Biological Activity", Annual Reports in Medicinal Chemistry 13: 227–238 (1978).

Matsuyama et al., "A Novel Extracellular Cyclic Lipopeptide Which Promotes Flagellum–Dependent and –Independent Spreading Growth of Serratia Marcescens", J. Bacteriol. 174: 1769–1776 (1992).

Mazerolles et al., "Regulation of T Helper–B Lymphocyte Adhesion Through CD4–HLA Class II Interaction"Eur. J. Immunol. 20: 637–644 (1990).

Mazerolles, et al., "Immunosuppressive Properties of Synthetic Peptides Derived from CD4 and HLA–DR Antigens"Cell 55:497–504 (1988).

McDonnell et al., "Rational Design of a Peptide Analog of the L3T4 CDR3–like Region"Immunomethods 1: 33–39 (1993).

Merrifield, "Solid Phase Peptide Synthesis. I. The Synthesis of a Tetrapeptide", J. Am. Chem. Soc. 15: 2149–2154 (1963).

Montefiori et al., "Evaluation of Antiviral Drugs and Neutralizing Antibodies to Human Immunodeficiency Virus by a Rapid and Sensitive Microtiter Infection Assay", J. Clin. Microbiol., 26: 231–235 (1988).

Padlan and Kabat, "Modeling of Antibody Combining Sites-",Meth. Enzym. 203: 3–45 (1991).

Perry et al., "Conversion of Immunity to Suppression by in Vivo Administration of I–A Subregion–Specific Antibodies", J. Exp. Med., 156: 480–491 (1982).

Pride et al., "Molecular Mimicry of Hepatitis B Surface Antigen by an Anti–Idiotype–Deprived Sythetic Peptide", Proc. Natl. Acad. Sci. USA 89: 11900–11904 (1992).

Ryu et al., "Crystal Structure of an HIV–Binding Recombinant Fragment of Human CD4", Nature 348: 419–426 (1990).

Salter et al., "A Binding Site for the T–Cell Co–Receptor CD8 on the $\alpha^3$Domain of HLA–A2", Nature 345: 41–46 (1990).

Saragovi et al., "Loops and Secondary Structure Mimetics: Development and Applications in Basic Science and Rational Drug Design", Biotechnology 10: 773–778 (1992).

Saragovi, et al., "Design and Synthesis of a Mimetic from an Antibody Complementarity–Determining Region", Science 253:792–795 (1991).

Saragovi and Greene, "Constrained Peptides and Mimetics as Probes of Protein Secondary Structure", Immunomethods 1 : 5–9 (1992).

Sibanda et al., "Conformation of β–Hairpins in Protein Structures", J. Mol. Biol. 206: 759–777 (1989).

Taub et al., "Peptide Sequences from the Hypervariable Regions of Two Monoclonal Anti–idiotypic Antibodies Against the Thyrotropin (TSH) Receptor Are Similar to TSH and Inhibit TSH–Increased cAMP Production in FRTL–5 Thyroid Cells", J. Biol. Chem. 267: 5977–84 (1992).

Taub et al., "A Monoclonal Antibody Against the Platelet FIbrinogen Receptor Contains a Sequence That Mimics a Receptor Recognition Domain in FIbrinogen", J. Biol. Chem. 264: 259–265 (1989).

Tramontano, et al., "Structural Determinants of the Conformations of Medium–Sized Loops in Proetins", Proteins Structure, Fuctions, and Genetics 6: 382–394 (1989).

Wang, et al., "Atomic Structure of a Fragment of Human CD4 Containing Two Immunoglobulin–Like Domain", Nature 348:411–418 1990).

Weiner et al., "Species Tropism of HIV–1 Infectivity of Interspecific Cell Hydribomas Implies Non–CD4 Structures Are Required for Cell Entry", Cancer Detection and Prevention 14: 317–320 (1990).

Weiner et al., "HIV Infectivity: Analysis of Viral Envelope Determinants and Target Cell Requirements for Infectivity by HIV–1", Vaccines 90:339–345 Cold Spring Harbor Laboratory Press (1990).

Welling et al., "A Ten–Residue Fragment of an Antibody (Mini–Antibody) Directed Against Lysozyme as Ligand in Immunoaffinity Chromatography", J. Chromatography 548: 235–242 (1991).

Welling et al., "Synthetic Antibody Fragment as Ligand in Immunoaffinity Chromatography", J. Chromatography 512: 337–343 (1990).

Williams, A., "A Year in the Life of the Immunoglobulin Superfamily"Immuno. Today, 8: 298–303 (1987).

Williams and Barclay, "The Immunoglobulin Superfamily–Domains for Cell Surface Recognition", Annual Review of Immunol., 6:381–405 (1988).

Williams, et al., "Contact Residues and Predicted Structure of the Reovirus Type 3–Receptor Interaction", J. Biol. Chem. 296:241–9250 (1991).

Williams et al., "Design of Bioactive Peptides Based on Antibody Hypervariable Region Structures", J.Biol. Chem. 266: 5182–5160 (1991).

Wood and Wetzel, "Novel Cyclization Chemistry Especially Suited for Biologically Derived, Unprotected Peptides", J. Pep. Prot. Res. 39: 533–539 (1992).

McMurray and Lewis, "The Synthesis of Cyclic Peptides Using Fmoc Solid–Phase Chemistry and the Linkage Agent 4-(4–Hydroxymethyl–3–methoxyphenoxy) –butyric Acid", Tetrahedron Letters 34: 8059–8062 (1993).

McMurray et al., "Cyclic Peptide Substrates of pp60$^{a-src}$"International Journal of Peptide and Peptide Research 42: 209–215 (1993).

CONSTRAINED PEPTIDES

FIELD OF THE INVENTION

The present invention relates to constrained peptides which exhibit high affinity to other molecules and/or enhanced biological activity.

BACKGROUND OF THE INVENTION

Intermolecular interactions involving proteins include receptor-ligand interactions, receptor-antigen interaction and antibody-antigen interactions. In each case, specific regions of the respective molecules involved in such interactions are involved. Often, regions of proteins involved in intermolecular interactions are loops.

In the case of proteins that are members of the immunoglobulin superfamily, such as antibodies and receptors, loops referred to complementarity determining regions (CDRs) are provided. The differences in sequence of CDRs are generated by alternative splicing of the genes encoding the protein at the region encoding the CDR. This alternative splicing generates a variety of CDRs on different antibodies and thereby allows for the diversity of targets for antibodies. Similarly, different T cell receptors bind to different antigens based upon the diversity of CDR sequences.

Williams, et al., (1988) *Annual Review of Immunol.*, 6:381–405, which is incorporated herein by reference, discloses that the numerous cell surface receptors that belong to the immunoglobulin gene superfamily share certain unique structural features. Antibodies, which are prototypes of the family, are composed of polypeptide chains whose amino acid sequences indicate the presence of homology regions of about 110 amino acids each. These regions fold into compact three-dimensional domains characterized by a β-barrel structure with an internal intradomain disulfide bond spanning approximately 65 amino acids. All members of the immunoglobulin gene superfamily are composed of one or several domains that share varying degrees of amino acid sequence homology. Williams, (1987) *Immuno. Today*, 8:298–303, which is incorporated herein by reference, discloses that the homology domains are often the product of a single exon.

Kappler, et al., (1987) *Cell*, 49:263–271, which is incorporated herein by reference, discloses that while the immunoglobulins bind to native antigens, the T cell receptors interact with antigenic fragments that have become associated with either class I or class II proteins which are themselves polymorphic members of the immunoglobulin gene superfamily. Bjorkman, et al., (1987) *Nature*, 329:506–511, which is incorporated herein by reference, discloses a peptide binding cleft deduced from the atomic structure of certain class I MHC proteins. The sides of the cleft are formed by two α helices and the bottom surface of the cleft is a β sheet. T cell receptor structures have not been determined but are likely to be similar to immunoglobulins in terms of their tertiary structure. The third hypervariable region of the α and β polypeptides of the T cell receptor may directly interact with antigen. (See Kappler, et al., supra; Bjorkman, et al., supra; and Fink, et al., (1986) *Nature*, 321:219, which are incorporated herein by reference.)

Other members of the immunoglobulin gene superfamily include the CD4, CD2 and CD8 molecules. Ryn, et al., (1990) *Nature*, 348:419–426, and Wang, et al., (1990) *Nature*, 348:411–418, each of which is incorporated herein by reference, disclose the three-dimensional structure of the protein engineered N-terminal domains of CD4 and CD8. The N-terminal half of the CD4 molecule is folded into two domains stabilized by disulfide bonds, reduction of which impairs the binding of the HIV protein gp120 to CD4. The CD4 domains are analogous to the complementarity determining regions (CDRs) of antibodies. CD4 has CDR2- and CDR3-like regions of anti-parallel β sheets connected by β turns. The CD4 molecule can interact with class II molecules; while the CD8 gene product, which is closely related to light chain gene segments, interacts with class I molecules. Leahy, et al., (1992) *Cell*, 68:1145–1162, which is incorporated herein by reference, discloses that the solution of the CD8 molecule revealed a very similar structure to that predicted by modeling of the sequence with the REI immunoglobulin structure. It is apparent that the portion of the CD8 molecule that has been analyzed to modest resolution (2.6 Å) is quite comparable with the CD4 structure as well. It has been possible to model which of the CDR loops of the CD8 molecule might bind to the class I structure. Modeling results suggest the centrally placed CDR2 loop attaches to the class I molecule. Likewise, using a different approach Fleury, et al., (1991) *Cell*, 66:1037–1049, which is incorporated herein by reference, has suggested that the CD4 CDR1 and CDR3 loops might be relevant to class II binding.

Fleury, et al., supra; Clayton, et al., (1988) *Nature*, 335:363–366; and Konig, et al., (1992) *Nature*, 356:796–798, each of which is incorporated herein by reference, disclose that part of the problem in studying large protein surface interactions by Alanine or site-directed mutagenesis is that introduction of hydrophobic or hydrophilic residues into the protein main chain at certain positions produces major conformational changes that cannot be anticipated without structural corroboration.

One study (Salter, et al., (1990) *Nature*, 345:41–46 which is incorporated herein by reference) has implicated a discrete loop of the α-3 domain of the class I molecule as part of the binding site for CD8, while Konig, et al. (1992) *Nature*, supra and Cammarota, et al., (1992) *Nature*, 356:799–800, which are incorporated herein by reference, have suggested an analogous structural motif on the β-2 domain of the class II molecule as a target for binding the CD4 ectodomain. Therefore, it is likely that both CD4 and CD8 use CDR-like loops to bind to other loop-like projections on the respective targets. Although T cell receptors can function in the absence of these CD4 or CD8 structures, they appear to play a critical role in some level of activation and ligation. In addition, they may also be important in some aspects of T cell development.

Amit, et al., (1986) *Science*, 233:747–753, which is incorporated herein by reference, discloses that molecular and crystallographic analysis of immunoglobulins has revealed that the critical ligand binding surfaces are CDR projections. In addition, it is apparent that there are canonical conformations of the complementarity determining regions of the V kappa light chain CDRs and two of the heavy chain CDRs. The third CDR of the heavy chain, as a consequence of the complex genetic mechanism which influences its structure, has medium or long loops which have diverse patterns of interactions. In general, the canonical CDRs, aside from the CDR3 of the heavy chain, have reverse turn conformations which can sometimes have the regular features of turns. (See Saragovi, et al. (1992) *Biotechnology*.) In addition, Williams, et al., (1988) *Annual Review of Immunol.*, 6:381–405 which is incorporated herein by reference, and Williams, *Immuno. Today*, supra, discloses that it is apparent that the C1 and C2 types of domains, while similarly fashioned from two β sheets linked together by a disulfide bond, serve as models of other β loop types and further disclose that the C1 domains are involved in antigen interactions, while C2 domains subserve Fc receptor and adhesive structures such as LFA-3, MAG, CD2 and NCAM and ICAM.

The conformational properties of peptide loops or reverse turns are considered important mediators in the biological activity of polypeptides. Turns provide for suitable orientations of binding groups essential for bioactivity by stabilizing a folded conformation in a small molecule and may be involved in both binding and recognition sites. See for example: Saragovi, et al., (1986) *Science*, 233:747–753; Chen, et al., (1992) *Proc. Nat'l Acad. Sci. U.S.A.*, 89:5872–5876; and Sibanda, et al., (1989) *J. Mol. Biol.*, 206:759–777, each of which is incorporated herein by reference. The studies of small naturally occurring peptides, such as somatostatin and encephalins, emphasized the role of turns in the optimal placement of side-chains for receptor binding and the influence of backbone conformations.

The field of synthetic peptides is one of intense activity, particularly the design of synthetic peptides useful to mimic biologically active proteins. A great deal of effort has been expended to identify the portion of a protein which is directly involved in intermolecular activity and to model small peptides based upon the amino acid sequence of that portion. Synthetic peptides are designed which are modelled upon the active regions of proteins. Such synthetic peptides may consist of identical sequences as that of the sequence of the protein which is involved in intermolecular interactions or they may comprise additional flanking amino acid sequences and/or include additions, deletions and/or substitutions within the sequence.

Linear synthetic peptides that are designed based upon the active portions of biologically active molecules, particularly loops, and more particularly CDRs, have achieved limited success. The biological activity of linear peptides which are designed based include regions that identical or substantially similar to active portions of biologically active molecules are often less than that of the biologically active protein. The reason for the diminished activity is that the linear peptides are not conformationally stable and shift from active to inactive conformations. Linear peptides are characteristically highly flexible molecules whose structure is strongly influenced by their environment, and their random conformation in solution may preclude their practical application to mediate binding and biological effects. Linear peptides often assume an aggregated state rather than an intramolecular folded state. It has been suggested that high conformational flexibility of small linear peptides and the volume to surface ratio are not favorable for proper folding (Marshall, et al. (1978) *Ann. Rep. Med. Chem.*, 13:227–238, which is incorporated herein by reference) and that this tendency precludes the use of short peptides as defined biological or therapeutic agents (Saragovi, et al., (1992) *Biotechnology*).

To address this reduction in activity, it is often desirable to provide conformationally restricted peptides. Conformationally constrained peptides which contain the biologically active loop have been designed and synthesized to provide peptides with loop regions which are conformationally restricted. Peptides are cyclicized or otherwise constrained by peptide or non-peptide bonds in order to maintain the active region in a stable and active conformation.

Williams, et al., (1991) *J. Biol. Chem.*, 266:5182–5190, and Williams, et al., (1991) *J. Biol. Chem.*, 296:9241–9250, each of which is incorporated herein by reference, describe the isolation and synthesis of conformationally constrained peptides derived from the complementarity determining regions of the light chain of antibodies. These constrained loops were analyzed to define the atomic basis of interaction of the individual residues with respect to binding. Four critical side chains at the tip of the loop were found to project into space and hydrogen bond with the target on the cell surface or to antibodies to which they bound. In addition, it was shown that it is possible to use the CDRs from immunoglobulins to develop constrained macrocyclic loops that have biological and antigen binding activities. Anti-receptor antibodies were utilized as a source of complementarity determining regions loop structures since the antibodies trigger a discrete biochemical response in cells upon ligating the receptor. In one set of studies, constrained peptides derived from the second CDR of the light chain of an anti-receptor antibody were shown to lead to an inhibition of lymphocyte DNA synthesis much like other immunologically active immunosuppressants.

Several examples of CDRs from anti-receptor antibodies acting as the major attachment sites of the antibodies were also disclosed. In these cases of anti-receptor antibodies, the residues of the antibody framework may be less important than in other foreign antigen binding immunoglobulins. This may be a consequence of the selection strategy of anti-receptor antibodies as opposed to antibodies to foreign antigens. The criteria for selecting anti-receptor antibodies is that they mediate a biological role independent of the binding properties. Consequently, selection is less biased by affinity considerations since even moderate affinity anti-receptor antibodies are adequate for most studies. In contrast, antibodies specific for soluble foreign antigens are usually selected for high affinity interactions.

Certain cyclic peptides are disclosed which demonstrate enhanced binding when compared to the corresponding linear peptides. These observations are consistent with the fact that critical ligand binding surfaces of immunoglobulins and related proteins are in a reverse turn conformation. Therefore, if a linear peptide is predicted to be more active in a turn configuration since it was derived from a known loop in the original protein structure, it can be subjected to cyclization. Cyclization can be readily achieved by the incorporation of cysteine residues during peptide synthesis, followed by oxidation. An intramolecular covalent disulfide bond is thus created which restricts the configuration of the peptide. An important consideration is the size or diameter of the loops obtained by cyclization. In order to develop insights into the diameter of the CDR loop studies were undertaken to constrain the loop and the orientation of the side chains. In one 16-mer, cysteine residues were introduced at random places to achieve a system of constrained loops. The cysteines placed at the 9th and 16th positions were far less effective at cyclization than cysteines placed in the 10 and 16th position. This indicates that small errors in spatial positioning can create compounds with reduced binding and biological activity. In addition, the constraint of the appropriately looped structures resulted in 40-fold higher levels of affinity than linear ones.

There is a need for improved synthetic peptides. There is a continue need for a means of increasing the biological activity of synthetic peptides designed based upon active regions of biologically active proteins. There is a need for conformationally restricted peptides which demonstrate improved biological activity. There is a need for conformationally restricted peptides which have enhanced affinity to the molecules that they interact with.

SUMMARY OF THE INVENTION

The present invention relates to aromatically modified constrained peptides. Aromatically modified constrained peptides are constrained peptides which have free aromatic amino acid residues linked to the constrained peptide.

The aromatically modified peptides of the invention comprise an amino acid sequence that consists of 30 amino acid residues and has the formula:

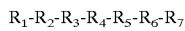

wherein:
- $R_1$ is 1–6 amino acid residues, at least one of which is tyrosine or phenylalanine;
- $R_2$ is a linking amino acid residue, preferably cysteine;
- $R_3$ is 0–13 amino acids;
- $R_4$ is an active sequence of 3–26 amino acids;
- $R_5$ is 0–13 amino acids;
- $R_6$ is a linking amino acid residue, preferably cysteine;
- $R_7$ is 1–6 amino acid residues, at least one of which is tyrosine or phenylalanine; and wherein $R_2$ and $R_6$ are bound to each other, thereby forming a cyclic portion which includes $R_2$, $R_3$, $R_4$, $R_5$ and $R_6$ with $R_1$ and $R_7$ forming exocyclic portions.

DETAILED DESCRIPTION OF THE INVENTION

As used herein, the term "biologically active protein" is meant to refer to a protein which interacts with another molecule, wherein such interaction is characterized by an affinity which, in some cases, may produce a signal and/or effect.

As used herein, the term "loop" is meant to refer to an amino acid sequence of a protein molecule that is interposed between either a) two alpha helices, b) two beta sheets or c) an alpha helix and a beta sheet.

As used herein, the term "biologically active loop" is meant to refer to an active region of a biologically active protein which is a loop and which is directly interacts with other molecules wherein the interaction is characterized by an affinity between the active region and the other molecule. CDRs of antibodies and CDR-like structures found in receptors are examples of biologically active loops.

As used herein, the terms "active sequence", "active portion of a biologically active protein" and "active region" are used interchangeably and are meant to refer to the amino acid sequence of the portion of a biologically active protein that is directly interacts with other molecules wherein the interaction is characterized by an affinity between the active portion and the other molecule. In some cases, the interaction between the active portion of a biologically active protein and the other molecule produces a signal or effect. Active sequences are often biologically active loops.

As used herein, the terms "conformationally restricted peptides", "constrained peptides" and "conformationally constrained peptides" are used interchangeably and are meant to refer to peptides which, for example through intramolecular bonds, are conformationally stable and remain in a sufficiently constant conformation to maintain the peptide's level of function and activity more consistently. Many conformationally restricted peptides whose structures are modeled upon the active region of a protein have been shown to have biological active similar to that of the protein.

As used herein, the terms "aromatic amino acids" and "aromatic amino acid residues" used interchangeably are meant to refer to phenylalanine and tyrosine.

As used herein, the term "exocyclic amino acid residue" is meant to refer to amino acid residues which are linked to cyclicized peptide but which are not within the portion of the peptide that makes up the circularized structure.

As used herein, the term "exocyclic portions" is meant to refer to an amino acid sequence having one or more amino acid residues which is linked to cyclicized peptide but which are not within the portion of the peptide that makes up the circularized structure.

As used herein, the term "linking amino acid residue" is meant to refer to an amino acid residue in an amino acid sequence which when linked to a non-adjacent amino acid residue results in cyclicizing at least a portion of the peptide.

The present invention relates to improved constrained peptides. Constrained peptides according to the present invention comprise a cyclic portion which comprises an amino acid sequence that directly interacts with other molecules and which further comprise amino acid residues that have aromatic groups, specifically phenylalanine and tyrosine, linked to, but outside of, the cyclic portion.

Constrained peptides are typically produced as linear peptides that are then cyclicized by non-peptide bonds, usually disulfide bonds between distally positioned cysteine residues, often N-terminal and C-terminal cysteines. According to the present invention, aromatic amino acid residues are provided as exocyclic amino acid residues in association with constrained peptides in order to provide increased interactions between the active sequence of the constrained peptide and other molecules. According to the invention, aromatic amino acids are exocyclic; that is, they are linked to the constrained peptides but are not within the cyclicized portion of the molecule.

The peptides of the present invention have the following features:

1) they consist of between 7 and 30 amino acids;
2) they are conformationally restricted such that they comprise a cyclic portion;
3) the cyclic portion includes an active sequence which consists of 3–18 amino acid residues;
4) the cyclic portion is linked to two exocyclic portions; and,
5) each exocyclic portion consists of 1–6 amino acids residues and comprises at least one aromatic amino acid residue.

Peptides of the invention comprise an amino acid sequence that consists of 7–30 amino acid residues. In some preferred embodiments, the peptides comprise an amino acid sequence that consists of 9–25 amino acid residues. In some preferred embodiments, the peptides comprise an amino acid sequence that consists of 12–20 amino acid residues. In some preferred embodiments, the peptides comprise an amino acid sequence that consists of 14–18 amino acid residues. In some preferred embodiments, the peptides comprise an amino acid sequence that consists of 10–16 amino acid residues.

Peptides may be constrained by any of several well known means. In preferred embodiments, disulfide bonds between two non-adjacent cysteines cyclicize and thereby conformationally restrict the peptide. The cyclization of linear peptides using disulfide bonds between non-adjacent cysteines is well known. Similarly, other non-adjacent amino acid residues may be linked to cyclicize a peptide sequence and the means to do so are similarly well known. Other methods of cyclization include those described by Di Blasio, et al., (1993) *Biopolymers*, 33:1037–1049; Wood, et al., (1992) *J. Pep. Prot. Res.*, 39: 533–539; Saragovi, et al., (1992) *Immunomethods*, 1:5–9; Saragovi, et al., (1991)

*Science,* 253:792–795; Manning, et al., (1993) *Reg. Peptides,* 45:279–283; Hruby, (1993) *Biopolymers,* 33:1073–1082; Bach, et al., (1994) *New Adv. Peptidomimetics Small Mol. Design,* I:1–26; and Matsuyama, et al., (1992) *J. Bacteriol.,* 174:1769–1776, each of which are incorporated herein by reference.

It is contemplated that the cyclized portion consists of 5 to 25 amino acid residues. In some preferred embodiments, the cyclized portion is 9 to 20 amino acid residues. In some preferred embodiments, the cyclized portion is 8 to 12 amino acid residues. In some preferred embodiments, the cyclized portion is 10 to 20 amino acid residues. In some preferred embodiments, the cyclized portion is 12 to 16 amino acid residues.

It is contemplated that the active sequence of the cyclized portion consists of at least 3 amino acid residues. In some preferred embodiments, the active sequence of the cyclized portion is at least 4 to 12 amino acid residues. In some preferred embodiments, the active sequence of the active sequence of the cyclized portion is at least 6 to 10 amino acid residues. In some preferred embodiments, the active sequence of the cyclized portion is at least 6 to 8 amino acid residues.

The active sequence of a constrained peptide is derived from a biologically active protein. There are numerous examples of active regions identified from biologically active proteins and constrained peptides which include active regions.

Generally, the active region is a biologically active loop which is either an antibody loop referred to as a complementarity determining region (CDR) or a CDR-like loop structure from a receptor or other member of the immunoglobulin superfamily.

Loops of proteins may be identified by those having ordinary skill in the art using well known molecular modelling techniques. According to such techniques, the three dimensional structure of a protein is calculated using X-ray crystallography data and/or computer software such as SYBIL. A detailed review is described in Tramontano, et al., (1989) *Proteins: Structure, Fuctions, and Genetics,* 6:382–394, and for members of the immunoglobulin family, see Davies, et al., (1990) *Annu. Rev. Biochem.* 1990:439–473, each of which are incorporated herein by reference. Those having ordinary skill in the art often superimpose the amino acid sequence of a protein of interest over the known three dimensional structure of a homologous or highly conservative protein to determine the approximate three dimensional structure of the protein of interest which can then allow for identification of the loop regions. Active loops of proteins and particular members of the immunoglobulin gene family may be identified using antibodies or by other means readily available to those having ordinary skill in the art, such as those taught by Tramontano et al., (1989) *Proteins: Structure, Fuctions, and Genetics,* 6:382–394, which is incorporated herein by reference.

CDRs are loops from antibodies which are involved in antigen recognition and binding. The amino acid sequence of CDRs may be ascertained by those having ordinary skill in the art using standard techniques. For example, the nucleotide sequence encoding an antibody may be sequenced and the sequence encoding the CDRs may be identified by routine means using, for example, computer assisted searching to locate hypervariable regions which encode CDRs as taught by Padlan, et al., (1991) *Meth. Enzym.,* 203:3–45, which is incorporated herein by reference.

Similarly, CDR-like structures from receptor proteins may be identified by either three dimensional molecular modelling techniques or by DNA sequencing of DNA molecules that encode the CDR-like structure using known sequences to locate regions that encode CDR-like sequences. (See Chen, et al., (1992) *Proc. Nat'l. Acad. Sci. U.S.A.* 89:5872–5876, which is incorporated herein by reference).

U.S. patent application Ser. No. 940,654, filed Sep. 3, 1992; U.S. patent application Ser. No. 702,833, filed May 20, 1991; U.S. patent application Ser. No. 326,328, filed Mar. 21, 1989; U.S. patent application Ser. No. 074,264, filed Jul. 16, 1987; U.S. patent application Ser. No. 462,542, filed Jan. 9, 1990; U.S. patent application Ser. No. 074,264, filed Jul. 16, 1987; U.S. patent application Ser. No. 648,303, filed Jan. 25, 1991; U.S. patent application Ser. No. 074,264, filed Jul. 16, 1987; U.S. patent application Ser. No. 685,881, filed Apr. 15, 1991; U.S. patent application Ser. No. 574,391, filed Aug. 27, 1990; U.S. patent application Ser. No. 194,026 filed May 13, 1988; U.S. patent application Ser. No. 074,264, filed Jul. 16, 1987; U.S. patent application Ser. No. 583,626, filed Sep. 14, 1990; each of which incorporated herein by reference, describe aspects of identifying active regions using anti-idiotype antibodies or anti-receptor antibodies. Taub, et al., (1989) *J. Biol. Chem.* 264:259–265; Taub, et al., (1992) *J. Biol. Chem.* 267:5977–84; Levi, et al., (1993) *Proc. Natl. Acad. Sci. USA* 90:437408; Pride, et al., (1992) *Proc. Natl. Acad. Sci. USA* 89:11900–4; Welling, et al., *J. Chromatography* 512:337–343; and Welling, et al., *J. Chromatography* 548:235–242, each of which is incorporated herein by reference, disclose identification of peptides which have active regions.

Constrained peptides may be improved by modifying them according to the present invention. Methods of synthesizing constrained peptides with modifications to place them within the scope of the present invention are well known and completely within the skill of those having ordinary skill in the art. Constrained peptides which mimic biologically active proteins are known. For example, cyclosporin is described in Merck Index, 10th Edition, page 396.

According to the present invention, the cyclic portion is linked to two exocyclic portions. Essentially, each exocyclic portion is an amino acid sequence consisting of 1–6 aromatic amino acid residues linked to the cyclic portion but not within the cyclicized conformationally restricted peptide. Each exocyclic portion extends out from the cyclic portion and comprises at least one aromatic amino acid residue. In some embodiments, each exocyclic portion consists of one amino acid residue. In some embodiments, one exocyclic portion consists of one amino acid residue and the other exocyclic portion consists of 1–6 amino acid residues. In some embodiments, one exocyclic portion consists of 1–3 amino acid residues and the other exocyclic portion consists of 1–6 amino acid residues. In some embodiments, each exocyclic portion consists of a single aromatic amino acid residue. In some embodiments, each exocyclic portion comprises a single aromatic amino acid residue.

It is preferred that the exocyclic residues are linked to the residues furthest from the active sequence. In some embodiments, it is preferred that the exocyclic residues occupy the N- and C-terminal positions and that the bonds are formed between the second and penultimate residues which cyclicized the remainder of the peptide, providing the N- and C-terminal residues as exocyclic residues.

In preferred embodiments the second and penultimate residues are cysteines which are linked by disulfide bonds. In preferred embodiments, one of either the N- and C-terminal residues is phenylalanine and the other is tyrosine.

The bonds which result in cyclization of a portion of the peptide are formed between one of the second, third, fourth, fifth, sixth or seventh residues and one of the penultimate, third to last, fourth to last, fifth to last, sixth to last residues or seventh to least residue. The binding of non adjacent residues forms the cyclized portion of the constrained peptide which has two exocyclic sequences of exocyclic amino acid residues between 1 and 6 residues each, respectively.

Peptides can be synthesized by those having ordinary skill in the art using well known techniques and readily available starting materials. According to the invention, references to synthesizing or constructing peptides is herein construed to refer to the production of peptides similar in sequence or structure to the corresponding regions identified by the method of the invention. These peptides may be produced using any method known in the art, including, but not limited to, chemical synthesis as well as biological synthesis in an in vitro or in vivo in a eukaryotic or prokaryotic expression system. In a preferred method, peptides of the invention are produced by solid phase synthesis techniques as taught by Merryfield, (1963) *J. Am. Chem. Soc.*, 15:2149–2154 and J. Stuart and J. D. Young, *Solid Phase Peptide Synthelia*, Pierce Chemical Company, Rockford, Ill. (1984), each of which is incorporated herein by reference.

Constrained peptides according to some embodiments of the invention have the formula:

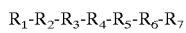

wherein:
$R_1$ is 1–6 amino acid residues, at least one of which is tyrosine or phenylalanine;
$R_2$ is a linking amino acid residue, preferably cysteine;
$R_3$ is 0–13 amino acids;
$R_4$ is 3–26 amino acids;
$R_5$ is 0–13 amino acids;
$R_6$ is a linking amino acid residue, preferably cysteine;
$R_7$ is 1–6 amino acid residues, at least one of which is tyrosine or phenylalanine;
and wherein $R_4$ is an active sequence and $R_1$, $R_2$ $R_3$, $R_4$, $R_5$, $R_6$ and $R_7$ taken together equal 30 amino acids or less.

Constrained peptides according to some embodiments of the invention have the formula:

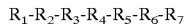

wherein:
$R_1$ is 1–3 amino acid residues, at least one of which is tyrosine or phenylalanine;
$R_2$ is a linking amino acid residue, preferably cysteine;
$R_3$ is 0–13 amino acids;
$R_4$ is 6–26 amino acids;
$R_5$ is 0–13 amino acids;
$R_6$ is a linking amino acid residue, preferably cysteine;
$R_7$ is 1–3 amino acid residues, at least one of which is tyrosine or phenylalanine;
and wherein $R_4$ is an active sequence and $R_1$, $R_2$ $R_3$, $R_4$, $R_5$, $R_6$, and $R_7$ taken together equal 30 amino acids or less.

Constrained peptides according to some embodiments of the invention have the formula:

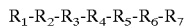

wherein:
$R_1$ is tyrosine or phenylalanine;
$R_2$ is a linking amino acid residue, preferably cysteine;
$R_3$ is 0–13 amino acids;
$R_4$ is 3–26 amino acids;
$R_5$ is 0–13 amino acids;
$R_6$ is a linking amino acid residue, preferably cysteine;
$R_7$ is tyrosine or phenylalanine; and wherein $R_4$ is an active sequence and $R_3$, $R_4$ and $R_5$ taken together equal 26 amino acids or less.

In some preferred embodiments, $R_1$ and $R_7$ are different amino acids such that if $R_1$ is tyrosine then $R_7$ is phenylalanine and if $R_1$ is phenylalanine then $R_7$ is tyrosine.

In some preferred embodiments, $R_4$ is 6–12 amino acid residues.

In some preferred embodiments, $R_3$ and $R_5$ are each, independently, 3–6 amino acid residues.

While $R_1$ and $R_7$ are linked to $R_2$ and $R_6$ by peptide bonds, it is contemplated that such residues can be linked by non-peptide bonds. It is also contemplated that other molecular structures which comprise aromatic rings may be used in place of aromatic amino acid residues that occupy $R_1$ and $R_7$.

EXAMPLES

Example 1

Constrained Macrocyclic Forms:

All of the compounds listed in Table I have been made and tested in a variety of studies. The compounds have been cyclized and modified at their termini with aromatic residues as described above to increase the enthalpic contribution of ordered water networks. HPLC purification has been performed to isolate several of the human compounds. All peptides were synthesized by solid-phase methods, deprotected, and released from the resin utilizing anhydrous HF. Peptides were lyophilized and further purified by high performance liquid chromatography utilizing two Delta-pack C18 columns and again lyophilized. Peptides (containing internal cysteine residues) were oxidized for experiments by dissolving them at 0.1 mg/ml in distilled water and stirring them for 3 to 5 days exposed to the air at 5° C. (Applied Biosystem Inc. 1991. Air oxidation protocol. An Introduction to cleavage techniques. Applied Biosystems, Inc., Foster City, Calif.).

The efficiency of the oxidation was tested by Ellman Determination. Determination of Free Sulfhydryls in peptides (Ellman Determination)-Peptides dissolved in $H_2O$ at 0.1 mg/ml were added at 30 $\mu$l to $NaPO_4$ 0.008 M, pH 8, and EDTA at 0.5 mg/ml for a final volume of 1 ml. To this was added 30 ml of 2,2'-bisazidothiobenzoic (Sigma chemicals) in 0.1 M $NaPO_4$, pH 8.0. This was allowed to react for 15 min, and the absorbance at 420 nm was then determined as described in Habeeb, A.F.S.A (1972) *Methods in Enzymology*, 25:457–464.

The sequences of the various loop regions in single letter code are disclosed in Table I.

TABLE I

| Compound | Sequence |
|---|---|
| CDR2-like | |
| CD4, 41–46 cyclized (SEQ ID NO:1) | Y, C, N, Q, G, S, F, L, C, Y-Human |
| CD4, 41–46 cyclized (SEQ ID NO:2) | F, C, N, Q, G, S, F, L, C, Y-Human |
| CD4, 47–52 cyclized (SEQ ID NO:3) | F, C, T, K, G, P, S, K, C, Y-Human |

TABLE I-continued

| Compound | Sequence |
|---|---|
| MHC II, 134–148 not cyclized (SEQ ID NO:4) | N, G, Q, E, E, K, A, G, V, V, S, T, G, L, I-Human |
| MHC II, 135–147 cyclized (SEQ ID NO:5) | F, G, Q, C, E, K, A, G, V, V, S, C, F-Human |
| MHC II, 134–145 not cyclized. (SEQ ID NO:6) CDR3-like | N, G, Q, C, E, K, A, G, V, V, S, C, G, L, I-Human |
| CD4, 84–91 cyclized (SEQ ID NO:7) | F, C, Y, I, C, E, V, E, D, Q, C, Y-Human |
| CD4, 87–93 cyclized (SEQ ID NO:8) | F, C, E, V, E, D, Q, K, E, C, Y-Human |
| CD4, 349–356 cyclized (SEQ ID NO:9) | F, C, L, S, D, S, G, Q, V, L, C, Y-Human |
| CDR2 form of 87.92.6 cyclized (SEQ ID NO:10) | F, K, T, N, K, C, I, Y, S, G, S, T, C, Q, F |

Example 2

CDR2 Loops:

Chen, et al. (1992) *Proc. Nat'l. Acad. Sci. U.S.A.*, 89:5872–5876, disclose the CDR2 region includes residues 40–50 and that a compound from the CDR2 loop interferes with gp120 binding to sCD4. Clayton, et al., (1989) *Nature*, 339:548–551, found that mutation of residue 48 of CDR2 disrupts MHC class II interaction. Fleury, et al., (1991) *Cell*, 66:1037–1049, using an identical approach however, found no such interference. The Clayton and Fleury studies dealt with the mutated holoreceptor while the Chen studies focused on a small surface of CD4. See also: Sibanda, et al., (1989) *J. Mol. Biol.*, 206:759–777; Mazerolles, et al., (1990) *Eur J. Immunol.*, 20:637–644; Mazerolles, et al., (1988) *Cell*, 55:497; and Doyle, et al ., (1987) *Nature*, 330:256–259.

Several loops have been designed and constructed to provide a constrained secondary structural form of the protein which incorporates parts of the 40–50 surface of the CD4 molecule compounds. These include SEQ ID NO:1, SEQ ID NO:2 and SEQ ID NO:3.

Example 3

CDR3 Constrained Peptides:

The CDR3-like region of CD4 is spatially separated from the CDR2 area. Fleury, et al., (1991) *Cell*, 66:1037–1049, discloses this region was not thought to be involved in direct high affinity binding to gp120. Furthermore, Fleury, et al., (1991) *Cell*, 66:1037–1049 and Mazerolles, et al., (188) *Cell*, 55:497, disclose that residues (Val 86, Glu 87, Asp 88 and Gln 89) at the tip of the CDR3-like domain have been implicated in some interactions. McDonnell, et al., (1993) *Immunomethods*, using a peptide analog of the L3T4 CDR3 region of CD4 employed proline-glycine-proline residues to create a tight turn of the region. The peptide was then analyzed using modeling and NMR. Unexpectedly, only 4 residues had spacial disposition features which were at all comparable with the residues seen in the authentic region of the CD4 molecule. These 4 residues, R,K,E,E, were localized to the descending lateral part of the loop and were thought to be responsible for the weak biologic activity noted (<mM).

Several loops have been designed and constructed to provide a constrained secondary structural form of the protein which incorporates parts of the CDR3-like region of the CD4 molecule. These include SEQ ID NO:7 and SEQ ID NO:8.

Example 4

Constrained macrocyclics have been evaluated for their ability to inhibit interactions between soluble CD4 (sCD4) and class II major histocompatibility complex (class II). We extended these biochemical studies to functional class II-T cell receptor interactions and gp120-CD4 interactions, T cell activation and inhibition of HIV mediated syncytia formation.

1) CD4 receptor-DRb2 Blocking:

A variation of the simple and elegant system developed by Cammarota, et al., (1992) *Nature*, 356:799–800, which is incorporated herein by reference, has been used to evaluate macrocyclic blocking. In the work described by Cammarota, sCD4 which is recombinantly produced and then radiolabelled is used to bind to a peptidic fragment of DRb2, residues 134–148 (SEQ ID NO:11—NGQEEKAGVVSTLGI). The peptidic fragment is first coupled to activated sepharose 4B (0.5 mg of peptide/ml of beads). Binding of the sCD4 to the peptide coupled beads is monitored and can be competed by 10 mg/ml of peptide.

75 $\mu$g of the recombinant soluble CD4 was labelled with 2 mCi of Bolotn Hunter reagent (Dupont/New England Nuclear) in 100 mM sodium borate, pH 8.5, in a volume of 150 $\mu$l. The labelled CD4 was separated from the unconjugated reagent on a G-50 Sephadex column containing PBS/ 0.1% gelatin and stored at -70° C. The specific activity was $2 \times 10^3$ cpm/$\mu$g.

HPLC purified forms of the DRb2 peptide were prepared. The peptide (10 mg/well in 0.1M ammonium bicarbonate, pH 7.8) was immobilized on Falcon microtiter plates by overnight exposure. After washing several times and blocking with 2% BSA in HBSS pH 7.6 for 2 hours we add 10 mg/well of $^{125}$I labelled sCD4. After 1 hour at room temperature the wells are washed 5× and the radioactivity counted.

Table II discloses the results observed over broad dose ranges. Certain of the tested compounds inhibit sCD4 binding to the human DRb2 residue with high specificity.

TABLE II

| Molecular forms are able to block sCD4 binding to DRb2 | | |
|---|---|---|
| Compound | Bound CD4 (cpm) | % inhibition of sCD4 binding |
| None | 3600 | 0 |
| SEQ ID NO:1 (.5 mg) | 3000 | 24 |
| SEQ ID NO:7 (.1 mg) | 2400 | 48 |
| SEQ ID NO:7 (.5 mg) | 1400 | 88 |
| SEQ ID NO:9 (.5 mg) | 4000 | 0 |
| no DRb2 added | 1100 | — |
| (Experiment 2) | | |
| none | 2000 | 0 |
| SEQ ID NO:7 | 800 | 100 |
| SEQ ID NO:5 | 1200 | 80 |
| no DRb2 | 1100 | — |

2) Inhibition of CD4 Binding to gp120 in vitro

To determine which compounds blocked CD4 interactions with gp120 an assay similar to that described by Chen, et al. (1992) *Proc. Nat'l Acad. Sci. U.S.A.*, 89:5872–5876 was used. This assay uses fluoresceinated gp120 and monitors its ability to bind to CD4+. The results are shown in Table III.

TABLE III

CD4 forms block F1-gp120 from binding to CD4+ human cells

| Compound (1 mg) | Mean Channel Fluorescence | % Inhibition |
| --- | --- | --- |
| None | 21 | 0 |
| SEQ ID NO:1 | 17 | 33 |
| SEQ ID NO:3 | 11 | 83 |
| SEQ ID NO:8 | 11 | 83 |
| SEQ ID NO:9 | 20 | 8 |
| SEQ ID NO:7 | 12 | 75 |
| Background fluorescence | 9 | 0 |

Recombinant gp-120 was obtained from Raymond Sweet at Smith Kline Beecham and directly fluoresceinated. Flow microfluorimetry was performed using a FACScan. Chen, et al., (1992) *Proc. Nat'l. Acad. Sci. U.S.A.*, 89:5872–5876; Weiner, et al., (1990) *Cancer Detection and Prevention*, 14:317–320; and Weiner, et al., (1990) *Vaccines*, 339–345, discloses the assay was done using the CD4 related synthetic compounds or, separately, monoclonal anti-CD4 antibody as described.

3) CD4 Forms Can Block T Cell Activation

TABLE IV

CD4 forms can block T cell activation

| Compound | $10^4$ T cells | tetanus toxoid | % response |
| --- | --- | --- | --- |
| none | + | + | 100 (45,090 cpm) |
| SEQ ID NO:1 | + | + | 77 (35,000 cpm) |
| SEQ ID NO:7 | + | + | 55 (25,000 cpm) |
| SEQ ID NO:9 | + | + | 100 (45,000 cpm) |
| none | + | − | 2 (1,000 cpm) |

$10^4$ blood monocytes were pulsed with 10 mg/ml of tetanus toxoid for 4 hours. $10^4$ CD4+ T cells were added with the compounds at 10 mg/ml in a final volume of 200 ml of media. The cells were pulsed with 1 mCi$^3$HTdR and assayed at 48 hours.

4) Blocking of the Mixed Lymphocyte Response.

TABLE V

Blocking of the mixed lymphocyte response

| Compound | (cpm) | % inhibition of MLR |
| --- | --- | --- |
| responder CD4+ T cells + allogeneic cells | 85,000 | 0 |
| SEQ ID NO:3 | 45,000 | 24 |
| SEQ ID NO:7 (.1 mg) | 55,000 | 48 |
| SEQ ID NO:8 | 20,000 | 88 |
| allogeneic cells alone | 200 | — |

Responder purified CD4+ T cells were used in a mixed lymphocyte response against completely allogeneic human cells. The compounds were added at 10 μg/ml final concentration. The number of responder cells was $10^5$ and the number of stimulators $4\times10^5$ cells per well.

5) Blocking of rgp120 Binding to CD4+Jurkat Cells

In previous studies, Chen, et al., (1992) *Proc. Nat'l. Acad. Sci. U.S.A.*, 89:5872–5876, HIV gp120 and its role in attachment and infection have been analyzed. According to the present invention, various forms of CD4 macrocyclics are used to block fluoresceinated recombinant gp120 in terms of binding to Jurkat CD4+ cells. Chen, et al., (1992) *Proc. Nat'l. Acad. Sci. U.S.A.*, 89:5872–5876, disclose the recombinant fluoresceinated-gp120 (FL-gp120) binds with moderate affinity to CD4+ Jurkat or Sup T1 cells.

6) Inhibition of HIV Infection in vitro

Chen, et al., (1992) *Proc. Nat'l. Acad. Sci. U.S.A.*, 89:5872–5876; Weiner, et al., (1990) *Cancer Detection and Prevention*, 14:317–320; and Weiner, et al., (1990) *Vaccines*, 339–345, disclose that certain CDR2 compounds have been studied for their effect on syncytia formation caused by HIV. Any compounds which block gp120 binding to Jurkat cells is assayed for activity in syncytia assays.

7) Syncytium Assays

Chen, et al., (1992) *Proc. Nat'l. Acad. Sci. U.S.A.*, 89:5872–5876; Weiner, et al. (1990) *Cancer Detection and Prevention*, 14:317–320, discloses Sup T1 cells are used as target cells because of their rapid and high degree of fusion when co-cultured with HIV-1 producing cell lines. Uninfected target cells were assayed by co-culture with HIV-infected cells (H9/IIIB.) Washed, HIV-infected cells are plated in 96-well plates ($10^4$ cells/well in RPMI 1640+10% FCS) and incubated for 30 min at 37° C. Target cells are then added at $5\times10^5$/well and the number of syncytia is qualitatively determined after a 48-hour incubation period. CD4 forms to be tested are added at time 0 or 24 hours after the assay has been initiated. Graded doses are used, controls including random linear peptides are also added independently. sCD4 and antibodies to CD4 are used as positive controls.

Another neutralization assay which is used in the field is as follows. One hundred TCID$_{50}$ of HIV-1/IIIB or HIV-1/MN cell-free virus is preincubated with serial dilutions of compounds for 1 hour at 37° C. Following incubation, the pretreated virus was then plated on $4\times10^4$ MT-2 target cells, for 1 hour at 37° C. The MT-2 cells were then washed 3 times and incubated at 37° C. with 5% $CO_2$. Fusion was evaluated 3 days later quantitatively by counting the number of syncytia per well in triplicate under a phase contrast microscope. The neutralization value (the ability of a compound to inhibit HIV infection 0 Vn/Vo) is calculated by dividing the mean number of syncytia per well following treatment with specific antiserum by the mean number of syncytia per well without antiserum (see: Montefiori, et al., (1988) *J. Clin. Microbiol.*, 26:231–235).

TABLE VI

Effect of various compounds on the syncytia forming ability of HIV strains. Strains examined HIV-1MN

| Compound | syncytia % | protection from syncytia |
| --- | --- | --- |
| None | 100 | 0 |
| SEQ ID NO:7 (6.125 μg) | 35 | 48 |
| SEQ ID NO:7 (12.5 μg) | 15 | 88 |
| SEQ ID NO:9 (.5 mg) | 55 | 0 |

Example 5

The effects of a modified CDR on cell activation and lymphoma cell growth are demonstrated as follows. The light chain of MAb 87.92.6, a monoclonal antibody specific for the cellular receptor for reovirus type 3 (Reo3R) is expressed in mouse R1.1 thymoma cells, rat B104 neuroblastoma cells and mouse L cells. Aggregation of cell surface Reo3R by CDR2 macrocyclic forms of the antireceptor light chains inhibits DNA synthesis, mimicking the immediate consequences of Reo3R binding by ligands such as pentameric 87.92.6 (IgM) or intact virus. DNA synthesis in concanavalin A-responsive splenocytes was also found to be inhibited peptides derived from complementarity determining region II (CDRII) of LC87 or a stereochemically constrained peptidomimetic of Reo3R ligands.

Reovirus serotypes 1 and 3 exhibit distinct tissue tropisms and interact with distinct cellular receptors. Type 1 reovirus infects ependymal cells which line the ventricles of the brain resulting in hydrocephalus without significant neuronal injury. Type 3 reovirus, in contrast, infects neurons resulting in a lethal encephalitis with extensive necrosis of cortical neurons. Determinants of viral tropism have been mapped to the reovirus s-1 protein, which mediates cell attachment and hemagglutination. Binding of type 3, but not type 1 reovirus inhibits DNA synthesis in cells which support infection of both serotypes. The receptor for type 3 reovirus (Reo3R) plays an important role in myelination in central and peripheral nervous systems and during T cell activation. Receptor aggregation is one step in the inhibition of DNA synthesis in Reo3R bearing cells. This effect is unrelated to viral replication since binding of UV inactivated virus or multivalent anti-Reo3R antibody can also inhibit cellular DNA synthesis.

An anti-receptor monoclonal antibody specific for Reo3R (MAb 87.92.6) was generated in which the light chain alone has been previously demonstrated to bear the determinants for Reo3R binding. The complementarity determining region (CDRII) of the k light chain of MAb 87.92.6 shares significant amino acid homology with the s-1 protein of type 3 reovirus between amino acids 317–332. Thus, the 87.92.6 light chain can be considered to be a surrogate for the type 3 reovirus s-1 cell attachment protein.

The cell-surface receptor recognized by the s-1 cell attachment protein of reovirus type 3 was initially characterized through the use of the anti-receptor MAb 87.92.6. Reo3R has been biochemically characterized as a glycoprotein consisting of two components, gp65 and gp95. The 65 kD component is a glycoprotein with a pI of 5.9 (5.8–6.1) with structurally similarities to the mammalian rhodopsin-beta-adrenergic receptor family of proteins. By several criteria, the catecholamine and reovirus binding sites appear to be distinct. Catecholamines and reovirus virions do not compete for binding to immunoprecipitated Reo3R or affinity-purified b2AR; and reovirus does not inhibit isoproterenol-induced cAMP accumulation in DDT1 cells. Thus, if the b2AR can serve as a Reo3R, the virus binds to a domain of the molecule distinct from the catecholamine binding site.

Binding of Reo3R ligands inhibit DNA synthesis in R1.1 cells and antigen activated or Concanavalin A activated T lymphocytes. The biological activity of the CDR2 macrocyclic SEQ ID NO:10 (F,K,T,N,K,C,I,Y,S,G,S,T,C,Q,F) was assayed using concanavalin A (ConA) mitogen stimulated splenocytes. The macrocyclic compound in synthesis in ConA-stimulated splenocytes in the same manner as treatment with MAb 87.92.6. Similar but less effective results were obtained using peptides derived from CDRII of LC87 or 87.1-mimetic, a conformationally restricted peptidomimetic of the CDRII of LC87.

The macrocyclic also inhibits proliferation of R1.1 thymoma cells (50%) but not with the same efficiency observed with Concanavalin A stimulated splenocytes (75–80%). The inhibition of concanavalin A-stimulated splenocyte proliferation by CDR2 macrocyclics was evaluated as follows. Briefly, BALB/c splenocytes were plated in 96 well microtiter plates at $10^5$ cells/well in complete RPMI1640 media containing 5 mg/ml ConA for 24 hours to allow expression of Reo3R. Macrocyclics were added at 10 $\mu$g/ml. The compound SEQ ID NO:10 (F,K,T,N,K,C,I,Y,S,G,S,T,C,Q,F) was added at 10 $\mu$g/ml and the cells were labelled with 1.0 mCi/well [$^3$H] thymidine for 18 hours. The plates were then placed at −20° C. until frozen. Cells were then thawed at room temperature and the incorporation of [$^3$H] thymidine was determined by hypotonic lysis and collection of the cellular DNA on glass fiber filters using a PHD cell harvester (Cambridge Technology Inc.). Shown are the mean ± standard deviation of 4–5 replicate determinations.

L cell cell lines and B104 cell were seeded into 96 well plates at $5\times10^4$ cells/well in 0.2 ml media. After 18 hours, polyclonal rabbit anti-mouse kappa light chain antisera, or normal rabbit serum were added (10 mg each as immunoglobulin) for 1 hour at 4° C. [$^3$H] thymidine (20 Ci/mmol, New England Nuclear) was then added at 1 mCi/well for the final 6 hours of culture at 37° C. For each cell line, the results of 3–5 replicate points shown are expressed as a percentage of the cpm (± standard deviation) incorporated following treatment with anti-k antisera relative to the cpm incorporated following treatment with the macrocyclic compound compared to linear forms.

TABLE VII

| Compound | (cpm) | % inhibition of proliferation |
|---|---|---|
| R1.1 cells - $10_4$ | 25,000 | 0 |
| SEQ ID NO:10 | 6,250 | 75 |
| linear form of SEQ ID NO:10 | 24,000 | 4 |

Example 6

The effects of the soluble cyclic macromolecules were examined in a model of inflammation and delayed hypersensitivity. The Azobenzenearsonate (ABA) hapten was used as a model antigen to study inflammation. The ABA hapten is coupled directly to cell surface proteins for presentation to T lymphocytes. As with other conventional antigens, it is necessary to prime animals with ABA-cells to induce an antigen specific immune response. Perry, et al., (1982) *J. Exp. Med.*, 156:480–491; Carroll, et al., (1987) *Immunology*, 62:471–475; and Lowy, et al., (1984) *Nature*, 308:373–374, disclose recognition of ABA by T lymphocytes has been shown to be MHC restricted. ABA peptides can be presented by class I and class II molecules for recognition by cytotoxic as well as helper T cells. Interestingly both anti-class II and anti-L3T4 monoclonal antibodies induce a state of hapten specific unresponsiveness when given at the time of priming with ABA hapten.

The effects of macrocyclics on in vivo inflammation were examined as follows. The effects of cyclic compounds disclosed in Table I on in vivo inflammatory response to Azobenzenearsonate was performed using treated groups of ABA primed normal Balb/c or Va3.1 transgenic mice with either 1) intravenously administered anti-CD4 monoclonal antibodies, 2) intravenously administered anti-class II antibodies, 3) systemically administered soluble forms of the most efficacious constrained macrocyclics 4) intravenously administered ABA coupled mononuclear cells, and 5) control antibodies and control macrocyclics.

100 mg of GK1.5 antibodies administered on days 0 and 1 completely abrogates in vivo priming for ABA. To compare the activity of the macrocyclics, 100 mg of the soluble macrocyclics were administered. The animals are assayed in vivo for DTH responses to ABA and their splenocytes restimulated in vitro for proliferative reactions. Studies of a macrocyclic compound modeled to bind to the reovirus receptor (CDR2R) on activated T cells have shown it to be efficacious at 100 μg total dose in reducing in vivo delayed type hypersensitivity to ABA.

Coupling of erythrocyte depleted splenocytes to ABA is performed as previously described by Perry, et al., (1982) *J. Exp. Med.*, 156:480–491; Carroll, et al., (1987) *Immunology*, 62:471–475; and Lowy, et al., (1984) *Nature*, 308:373–374. Briefly, a 40 mM solution of benzenearsonate diazonium is prepared from para-arsanilic acid (Eastman Kodak Co., Rochester, N.Y.) and reacted with erythrocyte depleted splenocytes at room temperature for 5 minutes. Coupling is stopped by addition of cold phosphate buffered saline, followed by several washes in Eagle's minimal essential medium (MEM). Coupling of erythrocyte depleted splenocytes to 2,4,6 trinitrobenzenesulfonic acid (TNBS) is performed by standard techniques.

The delayed type hypersensitivity assay is performed as follows. Five days after priming a mouse with hapten coupled cells, the hind left footpad is measured using an engineer's caliper (Fowler). Mice are challenged with 20 ml of active ABA diazonium salt solution injected into the footpad. Twenty four hours later, the degree of swelling is measured in the footpad. Perry, et al., (1982) *J. Exp. Med*., 156:480–491; Carroll, et al., (1987) *Immunology*, 62:471–475; and Lowy, et al., (1984) *Nature*, 308:373–374, disclose unimmunized mice are injected with ABA diazonium as a control for the effects of challenge.

For priming, mice (normal or transgenic with a T-cell receptor that recognizes ABA) are injected subcutaneously in each flank using a 23 g needle with 0.1 ml of ABA- or TNP-coupled spleen cells ($3\times10^7$). Five days later, ear thickness and footpad thickness is measured with a caliper. The mice are challenged on the ears (or footpads) by 1) painting with 20 ml of 0.7% picryl chloride (in 4:1 acetone:olive oil), 2) injecting 30 ml of ABA-diazonium salt in a balanced salt solution using a 30 g needle into the outer rim of the ear, or 3) injecting $5\times10^6$ allogeneic cells in Minimal Essential Media (30 ml) into the outer rim of the ear. If testing a single animal for three responses, one of the injections is in a footpad. Twenty four hours after challenge, the ears and footpads are measured and the animals sacrificed by cervical dislocation. Table VIII discloses results.

TABLE VIII

Inhibition of in vivo inflammation

| Compound | swelling ($10^{-2}$) | % inhibition |
|---|---|---|
| HBSS | 28 | 0 |
| SEQ ID NO:10. | 15 | 54 |
| linear form of SEQ ID NO:10 | 27 | 4 |

What is claimed is:

1. A constrained peptide having the formula:

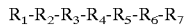

$$R_1\text{-}R_2\text{-}R_3\text{-}R_4\text{-}R_5\text{-}R_6\text{-}R_7$$

wherein:

$R_1$ is 1–5 amino acid residues, at least one of which is tyrosine or phenylalanine;

$R_2$ is a linking amino acid residue;

$R_3$ is 0 amino acid;

$R_4$ is an amino acid sequence comprising 3–8 amino acids, wherein the amino acid sequence is identical to the amino acid sequence of a complementarity determining region or a complementarity determining region-like structure of an immunoglobulin superfamily member;

$R_5$ is 0 amino acid;

$R_6$ is a linking amino acid residue;

$R_7$ is 1–5 amino acid residues, at least one of which is tyrosine or phenylalanine;

wherein:

$R_2$ and $R_6$ are linked to each other to form a cyclic portion of said constrained peptide consisting of $R_2\text{-}R_3\text{-}R_4\text{-}R_5\text{-}R_6$;

and $R_1$ and $R_7$ are exocyclic.

2. A constrained peptide according to claim 1 wherein $R_1$ is tyrosine or phenylalanine.

3. A constrained peptide according to claim 1 wherein $R_7$ is tyrosine or phenylalanine.

4. A constrained peptide according to claim 1 wherein $R_1$ is tyrosine or phenylalanine and $R_7$ is tyrosine or phenylalanine.

5. A constrained peptide according to claim 1 consisting of 10–16 amino acid residues.

6. A constrained peptide according to claim 1 wherein $R_2$ is cysteine and $R_6$ is cysteine.

7. A constrained peptide according to claim 1 wherein said peptide is selected from the group consisting of SEQ ID NO:1; SEQ ID NO:2; SEQ ID NO:3; SEQ ID NO:5; SEQ ID NO:7; SEQ ID NO:8 and SEQ ID NO:10.

8. A constrained peptide according to claim 1 wherein the amino acid sequence of $R_4$ is identical to the amino acid sequence of a complementarity determining region-like structure of CD4.

9. A constrained peptide according to claim 8 wherein $R_4$ is: NQGSFL, TKGPSK, YICEVEDQ or EVEDQKE.

10. A constrained peptide according to claim 8 wherein said peptide is selected from the group consisting of SEQ ID NO:1; SEQ ID NO:2; SEQ ID NO:3; SEQ ID NO:7; and SEQ ID NO:8.

11. A constrained peptide according to claim 1 wherein the amino acid sequence of $R_4$ is identical to the amino acid sequence of a complementarity determining region-like structure of an MHC molecule.

12. A constrained peptide according to claim 11 wherein $R_4$ is EKAGVVS.

13. A constrained peptide according to claim 11 wherein said peptide is SEQ ID NO:5.

14. A constrained peptide according to claim 1 wherein the amino acid sequence of $R_4$ is identical to the amino acid sequence of a complementarity determining region of an antibody.

15. A constrained peptide according to claim 14 wherein $R_4$ is IYSGST.

16. A constrained peptide according to claim 14 wherein said peptide is SEQ ID NO:9.

* * * * *

SEQUENCE LISTING

```
(1) GENERAL INFORMATION:

(iii) NUMBER OF SEQUENCES: 11

(2) INFORMATION FOR SEQ ID NO:1:

(i) SEQUENCE CHARACTERISTICS:
          (A) LENGTH: 10 amino acid residues
          (B) TYPE: amino acid
          (D) TOPOLOGY: unknown (xi) SEQUENCE DESCRIPTION: SEQ ID NO:1:

Tyr Cys Asn Gln Gly Ser Phe Leu Cys Tyr
                5                   10

(2) INFORMATION FOR SEQ ID NO:2:

(i) SEQUENCE CHARACTERISTICS:
          (A) LENGTH: 10 amino acid residues
          (B) TYPE: amino acid
          (D) TOPOLOGY: unknown (xi) SEQUENCE DESCRIPTION: SEQ ID NO:2:

Phe Cys Asn Gln Gly Ser Phe Leu Cys Tyr
                5                   10

(2) INFORMATION FOR SEQ ID NO:3:

(i) SEQUENCE CHARACTERISTICS:
          (A) LENGTH: 10 amino acid residues
          (B) TYPE: amino acid
          (D) TOPOLOGY: unknown (xi) SEQUENCE DESCRIPTION: SEQ ID NO:3:

Phe Cys Thr Lys Gly Pro Ser Lys Cys Tyr
```

5                   10

(2) INFORMATION FOR SEQ ID NO:4:

(i) SEQUENCE CHARACTERISTICS:
        (A) LENGTH: 15 amino acid residues
        (B) TYPE: amino acid
        (D) TOPOLOGY: unknown (xi) SEQUENCE DESCRIPTION: SEQ ID NO:4:

Asn Gly Gln Glu Glu Lys Ala Gly Val Val Ser Thr Gly Leu Ile
1               5                   10                  15

(2) INFORMATION FOR SEQ ID NO:5:

(i) SEQUENCE CHARACTERISTICS:
        (A) LENGTH: 13 amino acid residues
        (B) TYPE: amino acid
        (D) TOPOLOGY: unknown (xi) SEQUENCE DESCRIPTION: SEQ ID NO:5:

Phe Gly Gln Cys Glu Lys Ala Gly Val Val Ser Cys Phe
1               5                   10

(2) INFORMATION FOR SEQ ID NO:6:

(i) SEQUENCE CHARACTERISTICS:
        (A) LENGTH: 15 amino acid residues
        (B) TYPE: amino acid
        (D) TOPOLOGY: unknown (xi) SEQUENCE DESCRIPTION: SEQ ID NO:6:

Asn Gly Gln Cys Glu Lys Ala Gly Val Val Ser Cys Gly Leu Ile
1               5                   10                  15

(2) INFORMATION FOR SEQ ID NO:7:

(i) SEQUENCE CHARACTERISTICS:
        (A) LENGTH: 12 amino acid residues
        (B) TYPE: amino acid
        (D) TOPOLOGY: unknown (xi) SEQUENCE DESCRIPTION: SEQ ID NO:7:

Phe Cys Tyr Ile Cys Glu Val Glu Asp Gln Cys Tyr
1               5                   10

(2) INFORMATION FOR SEQ ID NO:8:

(i) SEQUENCE CHARACTERISTICS:
        (A) LENGTH: 11 amino acid residues
        (B) TYPE: amino acid
        (D) TOPOLOGY: unknown (xi) SEQUENCE DESCRIPTION: SEQ ID NO:8:

Phe Cys Glu Val Glu Asp Gln Lys Glu Cys Tyr
1               5                   10

(2) INFORMATION FOR SEQ ID NO:9:

(i) SEQUENCE CHARACTERISTICS:
        (A) LENGTH: 12 amino acid residues
        (B) TYPE: amino acid
        (D) TOPOLOGY: unknown (xi) SEQUENCE DESCRIPTION: SEQ ID NO:9:

Phe Cys Leu Ser Asp Ser Gly Gln Val Leu Cys Tyr
1               5                   10

(2) INFORMATION FOR SEQ ID NO:10:

(i) SEQUENCE CHARACTERISTICS:
        (A) LENGTH: 15 amino acid residues
        (B) TYPE: amino acid
        (D) TOPOLOGY: unknown (xi) SEQUENCE DESCRIPTION: SEQ ID NO:10:

```
Phe Lys Thr Asn Lys Cys Ile Tyr Ser Gly Ser Thr Cys Gln Phe
1               5                   10                  15
```

(2) INFORMATION FOR SEQ ID NO:11:

(i) SEQUENCE CHARACTERISTICS:
        (A) LENGTH: 15 amino acid residues
        (B) TYPE: amino acid
        (D) TOPOLOGY: unknown (xi) SEQUENCE DESCRIPTION: SEQ ID NO:11:

```
Asn Gly Gln Glu Glu Lys Ala Gly Val Val Ser Thr Leu Gly Ile
1               5                   10                  15
```